(12) United States Patent
Colle et al.

(10) Patent No.: US 9,551,671 B2
(45) Date of Patent: Jan. 24, 2017

(54) METHOD AND DEVICE FOR DETECTING, IN PARTICULAR, REFRACTING DEFECTS

(71) Applicant: MSC & SGCC, Vourles (FR)

(72) Inventors: Olivier Colle, Oullins (FR); Florence Drouet, Bures sur Yvette (FR); Marc Leconte, Loire sur Rhone (FR)

(73) Assignee: MSC & SGCC, Vourles (FR)

( * ) Notice: Subject to any disclaimer, the term of this patent is extended or adjusted under 35 U.S.C. 154(b) by 181 days.

(21) Appl. No.: 14/416,369

(22) PCT Filed: Jul. 18, 2013

(86) PCT No.: PCT/FR2013/051740
§ 371 (c)(1),
(2) Date: Jan. 22, 2015

(87) PCT Pub. No.: WO2014/016500
PCT Pub. Date: Jan. 30, 2014

(65) Prior Publication Data
US 2015/0204797 A1    Jul. 23, 2015

(30) Foreign Application Priority Data
Jul. 23, 2012  (FR) ...................... 12 57117

(51) Int. Cl.
*G01N 21/00* (2006.01)
*G01N 21/90* (2006.01)
(Continued)

(52) U.S. Cl.
CPC .......... *G01N 21/90* (2013.01); *G01N 21/8851* (2013.01); *G01N 21/958* (2013.01);
(Continued)

(58) Field of Classification Search
CPC ......... G02B 5/201; G02B 7/003; G02B 7/021; G02B 7/04; G02B 7/09; G02B 7/34; G01B 11/0608; G01B 11/24; G01B 9/02043; G01J 2005/0085; G01J 5/02
See application file for complete search history.

(56) References Cited

U.S. PATENT DOCUMENTS 5,004,909 A * 4/1991 Fukuchi ................. G01N 21/90
                                                            250/223 B
6,304,323 B1 * 10/2001 Ishikura ................. G01N 21/90
                                                            250/223 B
(Continued)

FOREIGN PATENT DOCUMENTS

DE    197 41 384    3/1999
EP    1 006 350    6/2000
(Continued)

*Primary Examiner* — Michael P Stafira
(74) *Attorney, Agent, or Firm* — Clark & Brody

(57) ABSTRACT

An in-line method for optically inspecting transparent or translucent containers (3) comprises illuminating each container with a light source that presents light intensity variation in a periodic pattern along at least a first variation direction. A number N greater than or equal to three of images of the container traveling in front of the light source and occupying N different respective positions along the travel path is taken. Between taking successive images, a relative shift between the container and the periodic pattern is created. A geometrical transformation is determined and applied in order to put the pixels belonging to the container in the N successive images of the same container into coincidence. A phase image for each container is constructed using the N registered images of the container. The phase image is analyzed in order to deduce therefrom at least the presence of defects or the quality of the container.

20 Claims, 4 Drawing Sheets

(51) Int. Cl.
*G01N 21/958* (2006.01)
*G01N 21/88* (2006.01)
(52) U.S. Cl.
CPC ........... *G01N 2021/8832* (2013.01); *G01N 2201/0484* (2013.01); *G01N 2201/062* (2013.01)

(56) References Cited

U.S. PATENT DOCUMENTS

2013/0120746 A1* 5/2013 Buchwald .............. G01B 11/25
356/239.4
2015/0204797 A1* 7/2015 Colle .................... G01N 21/90
356/239.4

FOREIGN PATENT DOCUMENTS

| EP | 1 498 725 | 1/2005 |
| FR | 2 794 241 | 12/2000 |
| FR | 2 907 553 | 4/2008 |
| FR | 2 958 040 | 9/2011 |
| FR | 2 958 751 | 10/2011 |

* cited by examiner

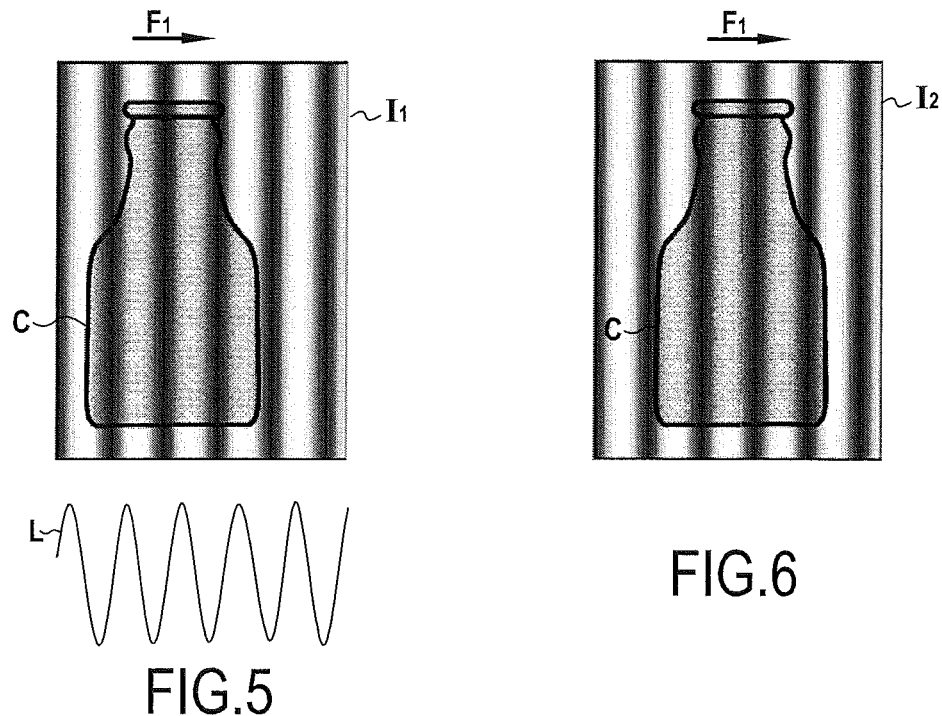
FIG.5
FIG.6
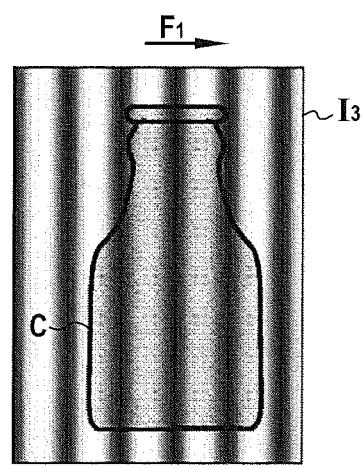
FIG.7

METHOD AND DEVICE FOR DETECTING, IN PARTICULAR, REFRACTING DEFECTS

The present invention relates to the technical field of in-line inspection of transparent or translucent containers such as for example bottles or jars, in order to determine characteristics presented by such containers for quality control purposes.

The present invention seeks in particular to inspect containers in order to detect any defects of the containers that present the characteristic of refracting or deflecting light, such as for example: defects of the crease, orange peel, whittle mark, crinkling, . . . types. In the description below, such defects are referred to as refractive defects or refraction defects.

In industrial fabrication of hollow glass containers by conventional methods such as press-and-blow or blow-blow processes, it is frequently observed that the thickness of the glass varies locally in the wall of the container, even for articles of simple shape such as cylindrical bottles. The outside surface that comes into contact with the mold during forming generally takes on the desired shape. As a result, variations in the distribution of glass and thus variations in the thickness of the wall give rise to deformations in the inside surface. When these variations are small, they have no consequence on the strength or on the appearance of the containers. In contrast, a bad distribution of material leads to appearances that can sometimes be troublesome, or worse there can even be certain places where there is no glass. It is considered that a good distribution of glass is a distribution that is uniform in thickness, such that the inner and outer surfaces are practically parallel throughout. In conventional methods, a poor distribution of glass is characterized and detected by measuring the thickness of the glass, where such measurements are generally localized or point measurements.

In the prior art, various solutions have been proposed for detecting defects in the refraction of light. For example, patent FR 2 794 241 proposes a machine adapted to detect defects of refraction without causing the container to turn.

That machine comprises a conveyor designed to bring the containers for inspection up to an inspection station. The inspection station has a camera situated on one side of the conveyor that is adapted to take an image of a container. The inspection station also has a light source situated on the other side of the conveyor and associated with means for defining light intensity that varies continuously in cyclical manner in space between dark and bright ends of the light source, with a rate of change that is less than that needed for detecting defects. Because of the lens effect, defects in the refraction of the container present the camera with portions of the light source that are in compressed form. Such a compressed image of the light source with intensity varying much more strongly increases the detection of a refractive defect by increasing its contrast.

In practice, that technique does not enable defects that refract light to be detected when they have low refractive power.

By way of example, another known technique is described in U.S. Pat. No. 5,004,909, it proposes a device for inspecting the walls of a container, the device comprising a camera for observing a light pattern through a container that is driven in rotation, the light pattern being made up of alternating white and black stripes. The deformations in the white and black stripes are analyzed in order to detect the presence of a defect that refracts light.

In practice, that technique is found to be very sensitive to the distribution of the material constituting containers. In the event of glass being distributed in a manner that is non-uniform but acceptable, the refractions caused by the slopes in the inner surfaces have the effect of deforming the patterns so that they become practically impossible to recognize, measure, or analyze in the images. Consequently, with such production, it would appear not to be possible to distinguish between refractive defects in containers and irregularities in the wall thickness of containers.

Also known, from patent application FR 2 907 553 are a method and a device comprising a light source that is controlled to produce a first type of illumination that is uniform and a second type of illumination made up of alternating dark zones and bright zones with discontinuous spatial variation. That device also has means for taking images of articles that are illuminated by the first and second types of illumination in order to detect respectively defects with high contrast and defects with low contrast.

Although such a device makes it possible to detect two types of defects using a single source, that device finds it difficult to detect certain types of refractive defect, mainly because only one image is taken with the second type of illumination. Defects with high contrast are detected using the uniform light source. In addition, defects with low contrast are detected with the single image obtained when the light source presents alternating black and white stripes with sharp edges and thus with discontinuous variations. In that image, deformations of the sharp edges of the stripy pattern and also local contrasts produced by the refractive defects are analyzed. When the container possesses variations in thickness and thus a poor distribution of glass, the deformations of the pattern are considerable and no longer enable defects with low contrast to be detected effectively.

Patent application FR 2 958 040 describes a method and an installation for detecting the presence and the height of defects in an optical component by producing a periodic light pattern that is transmitted through the optical component, by acquiring successive images of the periodic pattern in transmission through the component, the successive images being shifted in phase on each acquisition, in calculating phase images from those successive images, and in analyzing said phase images in order to deduce the presence of defects therefrom.

In practice, that technique is not adapted to in-line inspection of transparent or translucent containers traveling at a high rate between a light source and a system, since it requires the inspected articles to be stopped for a long period in order to enable a plurality of images to be acquired.

The present invention thus seeks to remedy the drawbacks of the prior art by proposing a novel technique for in-line inspection of transparent or translucent containers, which technique is adapted to detect at least defects that refract light, independently of the uniformity of material distribution.

Another object of the invention is to propose a method that enables containers that are moving in line at high speed to be inspected for the purposes of detecting with great reliability at least defects that refract light, and also of at least determining the quality of the distribution of the material constituting the containers.

In order to achieve such an object, the method of the invention provides in-line inspection of transparent or translucent containers traveling along a determined path $F_1$ at a high rate between a light source and an image-taking system for taking images of the containers and for analyzing the images taken in order to determine characteristics of the containers.

According to the invention, the following steps are performed:

illuminating each container traveling at a high rate by means of the light source that presents light intensity variation in a periodic pattern of period $T_1$ along at least a first variation direction;

for each container, taking a number N greater than or equal to three of images of the container traveling in front of the light source and occupying N different respective positions along the travel path;

between taking successive images, creating a relative shift between the container and the periodic pattern in a variation direction of the periodic pattern;

determining and applying a geometrical transformation in at least N−1 images of the same container for at least a set of points belonging to the container in order to put the pixels belonging to the container in the N successive images of the same container into coincidence;

for each container using the N registered images of the container, constructing a phase image; and analyzing the phase image in order to deduce therefrom, as a characteristic of the container, at least the presence of a defect that refracts light or the quality of the distribution of the material constituting the container.

The term "phase image" is used in the description below to mean an image, i.e. a two-dimensional table of pixel values, said values expressing the phase of the gray level variation of a pixel among the N successive images. The light passing through the containers is deflected as a result of the refraction effect, and this gives rise to a shift in said phase. The phase image thus contains information quantifying the refractive power of the containers through which the light passes.

Likewise, in the description below, the term "intensity image" designates an image, i.e. a two-dimensional table of pixel values, said values expressing a light intensity value. The light intensity image contains information quantifying absorption by the containers through which the light has passed, depending on their nature and their color.

Naturally, in reality, refraction can have an effect on an intensity image, but this effect cannot be measured accurately.

An advantage provided by the present invention is to enable the distribution of the material of containers to be characterized by the distribution and the intensity of the refractions produced by the inner and outer faces of the wall not being parallel, in other words by the resulting prism effects, or indeed more precisely by the slopes between the pairs of inner and outer surfaces of the containers.

The inspection method of the invention also includes in combination one and/or more of the following additional characteristics:

for each container, using the N registered images of the container to construct an intensity image and analyzing the intensity image in order to deduce therefrom, as a characteristic of the container, the presence of a defect that absorbs light and/or its dimensions;

in order to analyze the phase image, determining the speed and/or the amplitude of variation and comparing said speeds and/or amplitudes with thresholds in order to determine the presence of a defect that refracts light or the quality of the distribution of the material constituting the container;

in a variant implementation:

illuminating each container to be inspected with the help of a light source presenting light intensity variation in a periodic pattern of period $T_2$ in a second variation direction different from the first variation direction;

for each container, taking a number N greater than or equal to three of additional images of the article traveling in front of the light source and occupying three N respective different positions along the travel path;

between taking successive images, creating a relative shift between the container and the periodic pattern along the second variation direction of the periodic pattern of period $T_2$;

for each container, using the N registered images of the article to construct a second phase image; and analyzing the second phase image in order to determine, as a characteristic of the container, the presence of a defect that refracts light or the quality of the distribution of the material constituting the container.

selecting the period $T_1$, $T_2$ of the periodic pattern and the occurrences of the images taken in such a manner that the relative shifts of the container and of the periodic pattern along the variation direction of the periodic pattern are equal fractions of the period of the pattern under consideration;

obtaining the relative shift between the periodic pattern and the containers by the containers traveling relative to the periodic pattern that remains stationary;

obtaining the relative shift between the periodic pattern and the containers by causing the periodic pattern to shift between taking successive images;

triggering the taking of images and/or the shifting of the illumination pattern as a function of the positions of the containers traveling relative to the image-taking system so as to obtain predefined shifts;

selecting a periodic pattern presenting a function in the variation in the level of the emitted light along the variation direction that is sinusoidal;

positioning the periodic pattern in such a manner that a variation in light intensity occurs in at least one direction parallel to the travel direction of the containers; and selecting a periodic pattern that is rectilinear.

The method of the invention also consists, for each container and on the basis of the N registered images of the container, in constructing a so-called "intensity" image and in analyzing the intensity image in order to deduce therefrom, as a characteristic of the container, the presence of a defect that absorbs light, and/or in order to deduce its dimensions. In order to calculate the intensity image, it is necessary for each point belonging to the container to take into consideration the N gray level values of a coinciding pixel in each of the N registered images, and then to determine a resulting intensity, e.g. by taking the maximum and preferably the sum or the average of the N values. The intensity of the image as obtained in this way depends mainly on the absorption of light by the container. Light absorption defects such as inclusions or dirt are thus determined correctly. This intensity image is equivalent to the image that would be obtained with a uniform light source, i.e. without periodic pattern, as is conventionally used for inspecting transparent containers. Thus, in optimized manner, the invention makes it possible to determine characteristics that are associated with refraction by analyzing the phase image, and characteristics that are associated with absorption by analyzing the intensity image.

The invention also provides an installation for in-line inspection of transparent or translucent containers in order to determine characteristics of the containers, the installation comprising conveyor means for conveying the containers so that they travel through an inspection station made up of at least one light source placed on one side of the traveling containers and at least one image-taking system for taking images of the containers arranged on the other side of the containers, together with a unit for analyzing the images taken.

According to the invention:
the light source presents light intensity variation with a periodic pattern of period $T_1$ along at least a first variation direction;
an image-taking system is suitable for taking a number N greater than or equal to three of images of each container placed in front of the light source, with a relative shift being created between the container and the periodic pattern along a variation direction of the periodic pattern between taking successive images; and
the control and processor unit comprises:
means for determining and applying geometrical transformation in at least N−1 images of the same container in order to put into coincidence pixels of the container in the N successive images of the same container as put into register in this way;
means for calculating at least one phase image from N registered images of the container; and
means for analyzing the phase images in order to deduce therefrom, as a characteristic of the container, the presence of a defect that refracts light or the quality of the distribution of the material constituting the container.

The inspection installation of the invention also includes in combination one and/or more of the following additional characteristics:
the control and processor unit also includes means for calculating at least one intensity image from N registered images of the container obtained from the first image-taking system, and means for analyzing intensity images in order to deduce therefrom, as a characteristic of the container, the presence of a defect that absorbs light, and/or its dimensions;
in order to detect a defect that modifies the polarization state of light, the inspection installation includes:
a filter interposed between the containers and the light source to polarize light linearly in a first polarization direction or circularly in a first direction of circular polarization;
a second image-taking system suitable for taking a number N greater than or equal to three of images of each container placed in front of the light source;
a filter interposed between the containers and the second image-taking system for polarizing light linearly in the polarization direction orthogonal to the first or circularly in the direction of circular polarization that is opposite to the first; and
a control and processor unit comprising:
means for determining and applying a geometrical transformation in at least N−1 images of the same container coming from the first image-taking system in order to put into coincidence pixels of the container in the N successive images of the same container as put into register in this way;
means for calculating at least one intensity image from N registered images of the container coming from the second image-taking system; and
means for analyzing the intensity images in order to deduce therefrom, as a characteristic of the container, the presence of a defect that modifies the polarization state of light;
the periodic pattern of the light source is stationary, such that the relative shift between the periodic pattern and the containers is obtained by the containers traveling relative to the periodic pattern;
the periodic pattern of the light source is shifted between taking successive images in order to obtain the relative shifts between the periodic pattern and the containers;
the periodic pattern of the light source is positioned in such a manner that a variation in light intensity occurs along at least one direction parallel to the travel direction of the containers;
the light source is suitable for presenting a periodic pattern presenting a function for variation in the level of emitted light along its variation direction that is sinusoidal;
the image-taking system is associated with synchronizing means in order to be triggered as a function of the positions of containers relative to the periodic pattern of the light source; and
the control and processor unit controls the light source in such a manner that the periodic light pattern is shifted in a given direction for taking each image.

Various other characteristics appear from the following description made with reference to the accompanying drawings, which show embodiments of the invention as non-limiting examples.

FIGS. 5 to 7 are examples of images of a light source with a stationary periodic pattern, the images being taken in succession through a container that is moving linearly.

Figure 1:
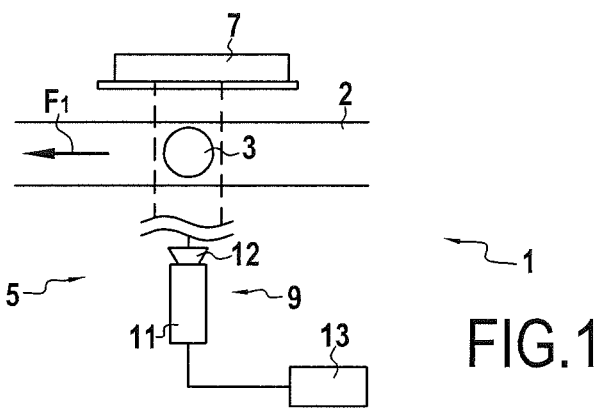
FIG. 1 is a plan view of an inspection machine performing the method in accordance with the invention.

As can be seen in FIG. 1, the inspection machine 1 of the invention comprises conveyor means 2 for conveying transparent or translucent containers 3 along a path designated by arrow $F_1$, i.e. a linear horizontal travel direction in the example shown. The containers 3 are conveyed upright or standing at a high rate, i.e. typically at a rate of 50 to 600 articles per minute, i.e. being conveyed at a speed that may be as high as 1.2 meters per second (m/s). The containers 3 are thus caused to pass in succession at a high rate in front of an inspection station 5.

The inspection station 5 has at least one light source 7 placed on one side of the conveyor means 2 and at least one image-taking system 9 for taking images of containers arranged on the other side of the conveyor means 2, there being specifically one such means in a first embodiment.

Thus, as can be seen more clearly in FIG. 1, while it is being conveyed, each container 3 is caused to travel between the light source 7 and the system 9 that takes images of the containers 3 in association with the light source 7.

The image-taking system 9 comprises at least one camera 11 having an objective lens 12 and connected to a control and image processor unit 13. The control and processor unit 13 serves to take and analyze images of the containers in order to deduce therefrom at least one characteristic of the containers. As explained in detail below, this control and processor unit 13 makes it possible to deduce, as a characteristic of the containers, the presence of a defect that refracts light and/or the quality with which the material constituting the container is distributed.

Advantageously, the camera 11 is adapted to take images of a container 3 over its entire height. For this purpose, the light source 7 has a light-emitting surface that is of sufficient size to back-light at least a portion of the observed field corresponding to the zone of the container that is to be inspected, and in particular the full height of the wall of the container. It should be observed that the inspection station 5 may have a plurality of image-taking systems combined with light sources in order to enable inspection to be performed over all or part of the circumference of a container while it is traveling in front of the inspection station 5.

According to a characteristic of the invention, the light source 7 presents a periodic pattern $7_1$ of light intensity variation that is appropriate for being transmitted through the container 3. The periodic light pattern $7_1$ is thus seen through the container 3 by transmission. The light source 7 presents a periodic light intensity pattern of period $T_1$ in at least a first variation direction D. The periodic light pattern $7_1$ of the light source as shown by way of example in FIGS. 2 to 4 corresponds to spatial variation in the intensity of the emitted light. Thus, various points of the light source 7 emit more or less light.

The variation in the light intensity (or overall contrast) of the light source 7 may extend from a dark level to a determined bright level of light, at least along the first variation direction. This variation in light intensity along this first direction is a periodic function, e.g. quasi-sinusoidal, and preferably sinusoidal. A non-sinusoidal periodic function could be used, although that presents the drawback of making phase calculation more complex and/or of requiring a larger number N of images to be acquired, and consequently of making the invention more expensive to use for in-line inspection of traveling transparent or translucent containers.

According to a preferred embodiment characteristic, the periodic pattern 7 presents sinusoidal variation of light intensity along the variation direction D. By way of example, and as shown in FIGS. 4 and 5, the direction D is horizontal and parallel to the axis $\underline{x}$, and the intensity or brightness values of the source along the direction $\underline{x}$ vary between a minimum $L_0-A$ and a maximum $L_0+A$ in application of a formula:

$$L(x)=L_0+A\sin(\omega \cdot x+\phi)$$

where:
 $L(x)$ is the intensity of light emitted at abscissa position $\underline{x}$;
 $L_0$ is mean intensity;
 A is amplitude of variation;
 $\omega$ is angular frequency;
 $\phi$ is phase at x=0.

Figure 2:
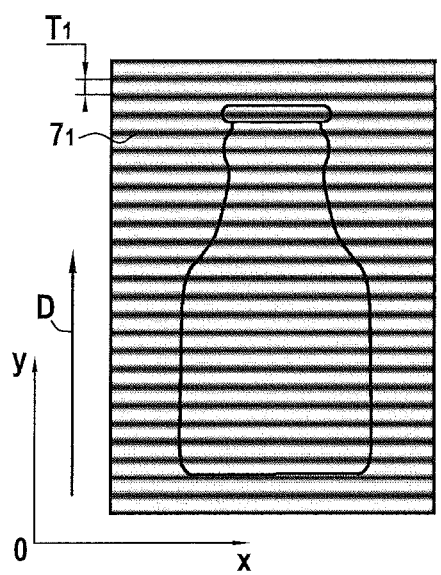
FIGS. 2 to 4 are elevation views of light sources in accordance with the invention presenting variations in light intensity that are respectively vertical, inclined, and horizontal.
Figure 3:
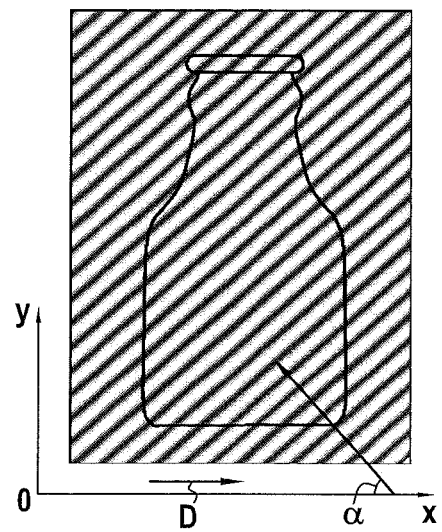
Figure 4:
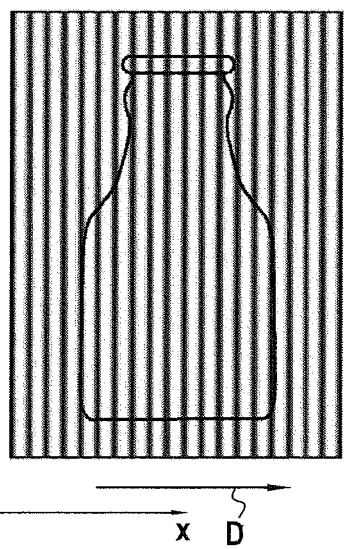

In the examples shown in FIGS. 2, 3, and 4, the periodic light pattern $7_1$ presents a structure of rectilinear light fringes. In FIGS. 2 and 4, the light source 7 presents light in the periodic pattern with intensity having maximum variation along the direction D and no variation in the direction perpendicular to the direction in which the rectilinear light fringes extend. In these embodiments, the periodic pattern presents variation in light intensity that is sinusoidal along the variation direction D. Thus, the light source 7 has a light intensity pattern $7_1$ constituted by a succession of alternating bright and dark rectilinear stripes or fringes.

In the description below, the light intensity variation direction D is considered relative to the horizontal and vertical directions in a 0, $\underline{x}$, $\underline{y}$ frame of reference. In the example shown in FIG. 2, the light variation direction D of the light source 7 corresponds to variation in light intensity being at a maximum when it is vertical (axis $\underline{y}$), such that the light intensity of the light source along the horizontal direction (axis $\underline{x}$) is constant. In the example shown in FIG. 3, the light intensity variation direction D of the light source 7 is at an angle of inclination a relative to the horizontal direction (axis $\underline{x}$). In the example shown in FIG. 4, the light intensity variation direction D of the light source 7 is shown parallel to the axis $\underline{x}$, such that in the vertical direction (axis $\underline{y}$) the light intensity of the light source 7 is constant.

In the examples shown in FIGS. 2 to 4, the light source 7 presents an array of light fringes that are parallel to a single direction. It should be observed that it is possible to envisage that the light source 7 presents fringes in a plurality of directions. Thus, the light pattern 7 could present fringes of other shapes such as curved shapes, concentric circles, chevrons, etc. Such complications to the light pattern presents an advantage in adapting detection sensitivity for various different regions of the article, on the assumption that detection is anisotropic because of the way the pattern is oriented.

The light source 7 is selected essentially as a function of the nature of the characteristics to be determined in the container and as a function of the shape of the containers, as can be understood from the description below.

According to an advantageous characteristic of the invention, it should be observed that the inspection station 5 may have a plurality of light sources with periodic patterns that present light intensity variations that extend in different directions.

The control and processor unit 13 control the camera 11 so as to take a number N of images of each container 3 that is placed in front of the light source 7, where N is greater than or equal to 3. For each image taken, the container 3 occupies a different position along the travel path $F_1$. Given that the containers 3 are traveling continuously in front of the camera 11, the acquisition of successive images by the camera is performed while the container 3 occupies different positions along its travel path $F_1$.

According to a characteristic of the invention, between acquiring two successive images, a relative shift is created between the container 3 and the periodic pattern $7_1$ along the variation direction D of the periodic pattern $7_1$. As explained in the description below, it is not essential for the relative shift between the container 3 and the periodic pattern $7_1$ to be perpendicular to the fringes.

In a first variant implementation, shown more particularly in FIGS. 5 to 7, the relative shift between the container 3 and the periodic pattern $7_1$ is obtained by the containers 3 traveling in front of the periodic pattern $7_1$, which remains stationary. In this preferred implementation, the natural travel of the containers 3 due to the conveyor means 2 is used, between taking two images, to create a relative spatial shift along the direction of the periodic pattern between the container 3 and the periodic pattern $7_1$ of the light source 7.

In the example shown in FIGS. 5 to 7, the periodic light pattern $7_1$ used is the pattern shown in FIG. 4. The periodic pattern $7_1$ is positioned relative to the container 3 so as to present a light intensity variation direction of the light pattern $7_1$ that is parallel to the travel direction $F_1$ of the container 3. In the example shown in FIGS. 5 to 7, the relative shift between the container 3 and the periodic pattern $7_1$ is considered to be horizontal, given that the travel path of the containers 3 is considered to be horizontal and taking place in the variation direction D of the periodic pattern $7_1$. FIGS. 5 to 7 show three images $I_1$, $I_2$, and $I_3$ taken in succession of the same container as it travels in front of the inspection station 5. In FIGS. 5 to 7, the container 3 is represented by its outline or envelope C.

A comparative analysis of the images $I_1$, $I_2$, and $I_3$ shown respectively in FIGS. 5 to 7 leads to the observation that the container 3 has been shifted along the travel direction $F_1$ of the container from one image to the next in front of the periodic pattern $7_1$, which remains stationary. The outline C of the container 3 is shifted (to the right) in the three successive images of FIGS. 5 to 7, given the travel direction $F_1$ of the container.

It should be considered that, with the container 3 traveling along a horizontal travel path, it is possible to envisage using a light source 7 having a periodic pattern $7_1$ that is different from the pattern shown in FIG. 4. Thus, provision may be made to use a light source 7 such as that shown in FIG. 3. In this example likewise, the periodic pattern $7_1$ is positioned relative to the container 3 in such a manner as to present a light intensity variation direction D of the light pattern $7_1$ that is parallel to the travel direction $F_1$ of the container 3. Thus, between taking two images, a relative shift is created between the container 3 and the periodic pattern along the variation direction D of the periodic pattern shown in FIG. 3.

In contrast, the light source 7 shown in FIG. 2 cannot be used if such a light source is stationary while the container travels along the travel direction $F_1$. There is no relative shift between the container 3 and the periodic pattern $7_1$ in a variation direction of the periodic pattern between taking two successive images. The light source 7 shown in FIG. 2 possesses light intensity that is constant along the travel direction $F_1$ of the container 3. It is necessary for the periodic pattern $7_1$ of the light source to be positioned in such a manner that, in the travel direction of the containers 3, the periodic light pattern $7_1$ possesses periodic variation of light intensity.

In a second variant implementation, the relative shift between the container 3 and the periodic pattern $7_1$ is created in a variation direction of the periodic pattern by shifting the periodic pattern $7_1$ between taking two images, and by the containers 3 traveling in front of the periodic pattern $7_1$. In this second variant implementation, the container 3 is moved in translation in front of the light source, and the periodic pattern $7_1$ is shifted between taking two images.

When the movement of the periodic pattern $7_1$ takes place along a horizontal direction (axis $\underline{x}$), the light source shown in FIG. 3 can be used. The light source shown in FIG. 3 can be used with a shift of the periodic pattern along the axis $\underline{x}$ or along the axis $\underline{y}$.

Naturally, it is possible to envisage moving the periodic pattern $7_1$ in a travel direction that is different from the horizontal axis, such that the light source 7 shown in FIG. 2 can be used. Thus, the light source 7 shown in FIG. 2 can be used when the travel direction $F_2$ of the light source $7_1$ is along the vertical direction (axis $\underline{y}$), i.e. parallel to the direction in which the periodic pattern varies.

The periodic pattern of the light source 7 may be shifted by any appropriate means. Thus, provision may be made to switch on and off point light sources, such as light-emitting diodes (LEDs). Likewise, it is possible to use a liquid crystal display (LCD) type screen placed in front of a uniform light source and to generate the periodic light pattern $7_1$ thereon, or else to use a video projector to light or back-light a screen.

The control and processor unit 13 uses the camera 11 to acquire in transmission through each container 3 at least three and preferably five images of the container, there being a relative shift between the container and the periodic pattern between taking the successive images, this shift being in a direction D in which the periodic pattern varies. Thus, for each container 3, the control and processor unit 13 has at least three images in which the periodic pattern $7_1$ is shifted in phase relative to the container.

The control and processor unit determines and applies a geometrical transformation to at least N−1 of these images of the same container for at least one set of points belonging to the container in order to bring into coincidence the pixels that belong to the container in the N successive images of the same container.

The control and processor unit 13 then constructs a single image for each container 3 on the basis of the N images of the container 3, e.g. in the manner described in patent EP 1 980 843. Naturally, for each container 3, a phase image can be calculated from N images of the container using various techniques.

In order to calculate the phase image of the container, it is necessary, for each point forming part of the container, to take into consideration the N values of a coinciding pixel in each of the N images (e.g., if N=3, in $I_1$, $I_2$, and $I_3$), and then to determine the phase of at least each point of the container from the N gray scale values taken in the N images, said values being modified by the relative shift between the periodic pattern and the container, and the calculated phase values depending on deflections or refractions of the light ray from the point under consideration of the container.

It should be observed that insofar as the container 3 is moving and the field of the camera is constant while taking the N images, the container 3 is situated in different positions in the N images taken in succession and is thus shifted because of the articles traveling through the field. For each point of the container, in order to obtain the N pixel values taken in the N images, it is appropriate to put said pixels belonging to the container into coincidence in the N successive images. The invention thus seeks in at least N−1 images of the same container to locate the container or its outline C, and then to determine and apply a geometrical transformation so as to bring the pixels belonging to the container into coincidence in the N successive images of the same container.

Figure 8:
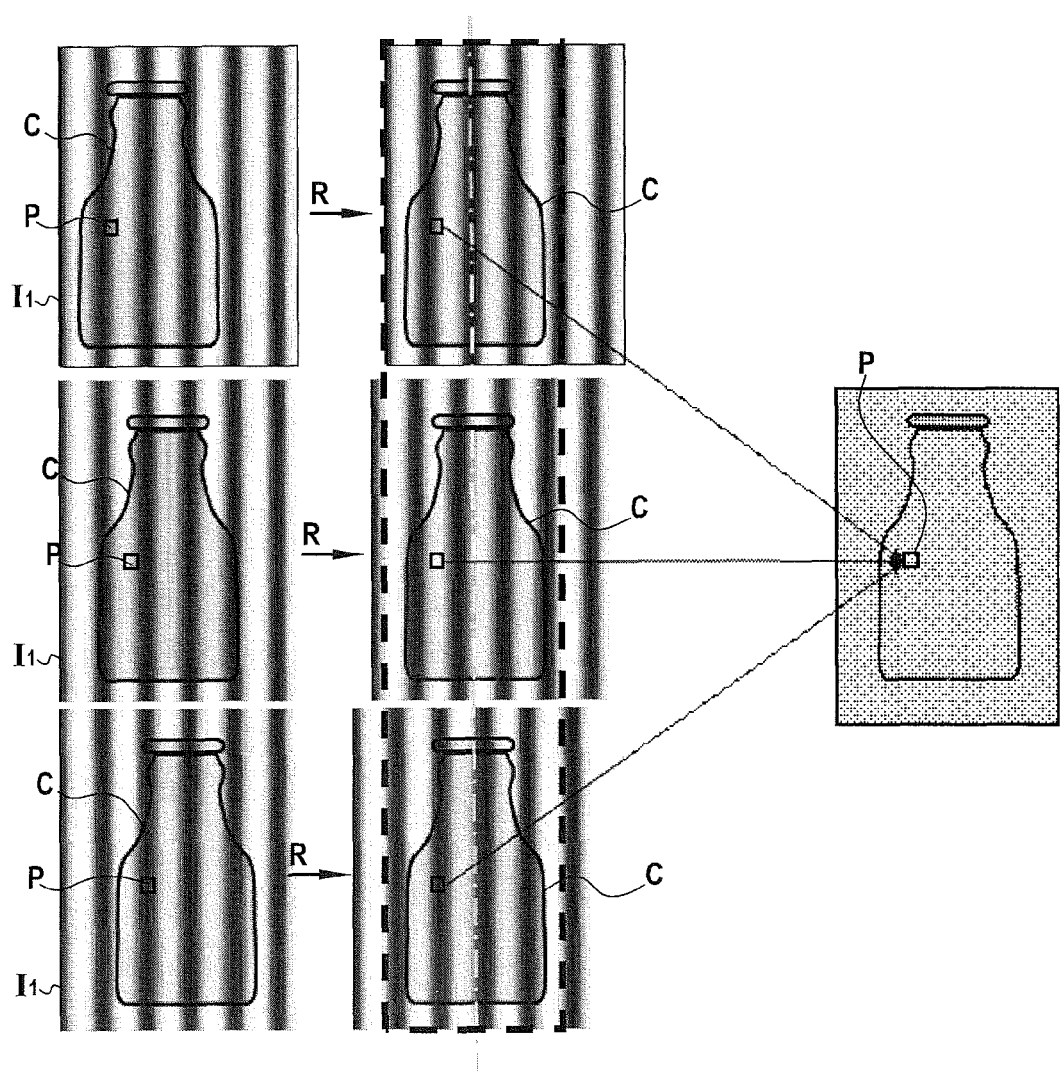
FIG. 8 shows an example of three images to which a registration operation is applied.

FIG. 8 shows an example for illustrating the registration or putting into coincidence of the pixels belonging to the same container and found in three successive images $I_1$, $I_2$, and $I_3$. A comparative analysis of the three images $I_1$, $I_2$, and $I_3$ shown in the left-hand portion of FIG. 8 reveals that the outline C of the container or a given point P of the container is shifted to the right in the images $I_1$, $I_2$, and $I_3$. In other words, the coordinates of the point P in the images $I_1$, $I_2$, and $I_3$ are different.

The right-hand portion of FIG. 8 shows the three images after the operation R of registering or putting into coincidence the pixels belonging to the container. This operation enables the outline C to be centered and consequently enables the point P to be put into register in the there images $I_1$, $I_2$, and $I_3$ so that the coordinates of the point P are identical.

Thus, the control and processor unit 13 has means for determining and applying a geometrical transformation in at least N−1 images of the same container in order to cause the pixels belonging to the container to be put into coincidence in the N successive images of the same container.

Once this registration has been done, for each point of the container, the variation in its gray scale in the N images is known and corresponds to the relative shift of the pattern. It is thus possible to calculate the phase of each point of the container. Said geometrical transformation comprises at least one shift in translation. Said geometrical transformation may be predetermined, or it may be calculated for each image on the basis of the location of a container in the image.

Said geometrical transformation may be applied to an entire image I, to an optionally rectangular region that includes the image of the container, or indeed only to pixels belonging to the container, i.e. to the region of the image that is defined by the outline C of the container, as in FIGS. 5 to 7.

One solution for registering images, when the physical movement of the container between images is known, is to calibrate the movement in pixels in the image and to shift the images in translation by the value of this movement.

Another solution consists in automatically detecting fixed points of interest on the containers (e.g. their edges) in the N images and in determining a geometrical transformation that enables those points of interest to be put into register, and then applying the same transformation to the entire container or to the entire image.

From N images of the same container that have been acquired and registered, the phase image is calculated as mentioned above. For each container, the control and processor unit 13 has N images that are separated by a phase shift that is preferably constant. A phase calculation algorithm is applied individually to each point of the container. Which particular phase calculation algorithm is selected from the various algorithms that are available depends specifically on the container, on the periodic pattern, on the speed of calculation, on the desired accuracy, etc.

Figures 9A, 9B, 9C:
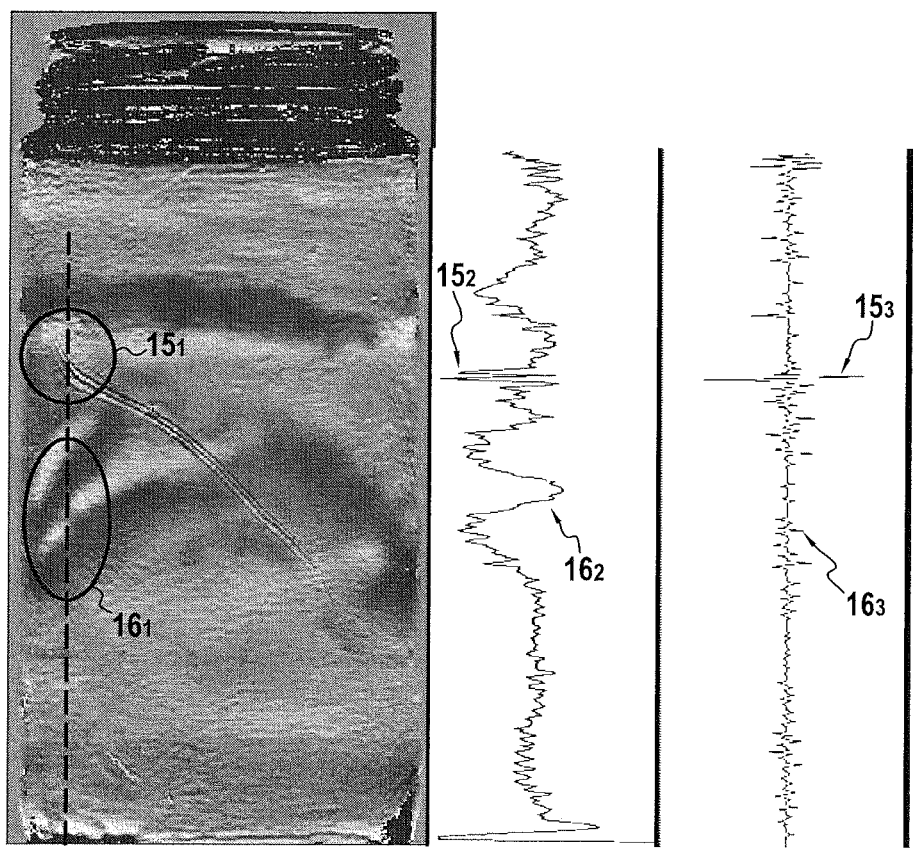
FIG. 9A shows an example of a phase image that has been deployed and then differentiated for revealing a defect that refracts light.
FIG. 9B shows the values of the signal of the image shown in FIG. 9A and taken along the column of the image, as represented by reference 14.
FIG. 9C shows the result of processing the signal shown in FIG. 9B with a high-pass filter.

It should be observed that, after the operation seeking to construct a phase image for each container, it is possible to envisage performing an optional operation of deploying the phase. Because of the periodicity of the light source 7, the phase that is obtained is also periodic, such that its value is defined solely between −π and π. Deploying the phase may be envisaged in order to eliminate jumps of 2π in order to obtain absolute phase. FIG. 9A shows an example of said differentiated absolute phase image.

Thereafter, the control and processor unit 13 analyzes each phase image, and more precisely analyzes phase variations in order to deduce therefrom at least one characteristic of the container 3. In a first variant implementation, the analysis of the phase image consists in determining the speed and/or the amplitude of the variation of the signal in the phase image and in comparing the speeds and/or amplitudes with thresholds in order to determine whether a defect that refracts light is present or in order to determine the quality with which the material constituting the container is distributed. The processing of each phase image may be performed using various known methods. For example, provision may be made to detect local phase variations (or shifts), by comparing the phase of each point of the image with the phase of neighboring points. Another technique consists in calculating a phase variation slope at each point and in comparing the results at each point with a threshold value. This variation slope may be calculated along one or more appropriate directions.

If phase variation is fast and of amplitude greater than a given threshold, then at least one characteristic of the container can be deduced therefrom, namely the presence of a defect that refracts light. If phase variation is slow and of amplitude greater than a given threshold, then at least one other characteristic of the container can be deduced therefrom, namely the distribution of the material constituting the container.

In a second variant implementation, the phase image is subjected to frequency analysis, making it possible to select variations as a function of their spatial frequency and thus to detect the presence of light refracting defects and possibly even to assess the quality of the skin of the glass by using the amplitude of high frequencies and the quality of material distribution by using the amplitude of low frequencies.

Phase variations depend directly on deflections or refractions of light by the container under the effect of refracting defects and of glass distribution.

FIG. 9A shows an example of a phase image that has been deployed and then differentiated serving to reveal a defect that refracts light. In the image of FIG. 9A, reference $15_1$ indicates the reference of a crease in the container. Reference $16_1$ indicates slow phase variations that are due to light being deflected by non-uniform distribution of glass as revealed by regions that are bright and regions that are dark.

The refracting defect, namely the crease $15_1$ in the example described, is easily located by its signature $15_2$ that appears in the image signal shown in FIG. 9B as taken along the image column given the reference 14. The refractive defect gives rise to steep local variation slopes in the signal. In this signal of the image taken along the column 14, slow variations can be seen that are associated with the non-uniform distribution of glass, these slow variations being identified by reference $16_2$ in the signal of FIG. 9B.

FIG. 9C shows the result of processing the signal shown in FIG. 9B by means of a high-pass filter. The defect $15_1$ appearing in the image of FIG. 9A is easily detectable in the signal shown in FIG. 9C (reference $15_3$) since the amplitude of local variations in the signal is large.

In this signal shown in FIG. 9C, the reference $16_3$ identifies the slow variations associated with the non-uniform distribution of glass. It should be observed that the non-uniform character of the distribution of glass does not interfere with detecting the refractive defects since this non-uniform distribution of glass does not produce changes in the signal, as can be seen in the vicinity of reference $16_3$.

It should be considered that the periodic pattern $7_1$ is observed through the containers and thus in the central zone is observed through four successive optical interfaces: air-glass, glass-air, air-glass, and glass-air, corresponding to four surfaces that are respectively outer, inner, inner, and outer, and through which the light passes. Since these surfaces are not uniformly parallel with one another because of the non-uniform distribution of material, and because of the presence of surface defects, bubbles, etc. . . . , they deflect light like prisms. The periodic light pattern $7_1$ is deformed thereby when it is observed through the transparent container. Unlike techniques seeking to detect only the deformation of patterns and the appearance within patterns of points or zones of local contrast, the phase shift makes it possible to calculate phase that is a measure of the deflections to which the light rays have been subjected, thereby making fine and discriminating analysis possible leading to characterizing the refracting power of defects and the quality of material distribution.

In the above-described examples, provision is made to illuminate each container with the help of a light source presenting light intensity variation along a variation direction D. In another variant implementation, it should be observed that it is possible to envisage illuminating each container with the help of a light source presenting light intensity variation in a periodic pattern of period $T_2$ in a second variation direction that is different from the first variation direction D. Thus, by way of example, it is possible to make provision for illuminating each container with the help of light sources having the periodic patterns shown in FIGS. 2 and 4. In this variant implementation, the method of the invention consists:

for each container, in taking a number N greater than or equal to three of additional images of the object traveling in front of the light source presenting a periodic pattern of period $T_2$, while the container is occupying N respective different positions along its travel path;

between taking successive images, in creating a relative shift between the container and the periodic pattern along the second variation direction of the periodic pattern of period $T_2$;

from the N images of the object, in constructing for each container a second phase image; and in analyzing the second phase image in order to detect phase variations that are greater than or less than a determined threshold in order to deduce therefrom whether a defect is present in the container.

According to an advantageous implementation characteristic, it should be observed that the period of the periodic pattern $7_1$ and also the occurrence of images and/or shifts of the pattern on the controlled source are selected in such a manner that the shifts relating to the container 3 and to the periodic pattern $7_1$ in the variation direction of the periodic pattern can be expressed as equal fractions of the period of the periodic pattern under consideration. For example, in the variant in which it is only the travel of the articles that creates the shift of the pattern relative to the container, and when five (N=5) images are taken, each image is taken so as to be shifted by one-fifth of the period of the periodic pattern $7_1$, i.e. the shift between each of the images taken is one-fifth of said period.

According to an advantageous implementation characteristic, the control and processor unit 13 controls the light source 7. The control and processor unit 13 can control the light source 7 in such a manner that the periodic light pattern $7_1$ is shifted in a given direction for each image taken. By way of example, for this purpose it may address an LCD screen, a video projector, LED circuits, or any other appropriate light source.

According to an implementation characteristic, the control and processor unit 13 triggers image acquisitions as a function of the precise position of the container in front of the light source 7. For this purpose, the control and processor unit 13 may be connected to presence and/or movement sensors such as incremental coders and cells.

In a second embodiment of the inspection station, the control and processor unit 13 also has means for calculating at least one intensity image from the N registered images of the container obtained by the image-taking system 9, together with means for analyzing intensity images in order to deduce therefrom, as a characteristic of the container 3, the presence or absence of a defect that absorbs light, and/or the dimensions of the container.

In a third embodiment, the inspection station includes a filter interposed between the containers 3 and the light source 7 for polarizing light linearly in a first polarization direction, or circularly in a first direction of circular polarization. The inspection station also includes a second image-taking system 9 analogous to the first image-taking system and suitable for taking a number N greater than or equal to three images of each container placed in front of the light source. The station also has a filter interposed between the containers 3 and the second image-taking system, for polarizing light linearly in the polarization direction that is orthogonal to the first direction or circularly in the direction of circular polarization that is opposite to the first direction of polarization rotation. In this example, the control and processor unit 13 also comprises:

means for determining and applying a geometrical transformation in at least N−1 images of the same container coming from the second image-taking system, in order to put into coincidence the pixels belonging to the container in the N successive images of the same container as put into register this way;

means for calculating at least one intensity image from the N registered images of the container coming from the second image-taking system; and means for analyzing the intensity image in order to deduce therefrom the presence or absence of a defect that modifies the polarization state of light and that constitutes a characteristic of the container 3.

It is known to use polarized light for detecting so-called "stress" defects, i.e. localized internal stresses in the glass that are of thermal or mechanical origin. For example, while a container made of glass is cooling a foreign body gives rise to stresses in the glass surrounding it. Because of the birefrigence of glass, such stresses modify the polarization state of light passing through the material. The presence of stress defects can thus be determined by combining a polarized light source on one side of the container and observing it in transmission through a polarizing filter that is orthogonal to the first. The person skilled in the art has no difficulty in performing the same detection when using circular polarization.

The combination of the various embodiments of the invention makes it possible to use a single light source and only two image-taking systems for determining, as a characteristic of the container 3, the presence or absence of a defect that refracts light, the quality with which the material constituting the container is distributed, the presence or the absence of a defect that absorbs light, the presence or the absence of a defect that modifies the polarization state of light, and/or the dimensions of the container.

The invention claimed is:
1. A method of an in-line method of optically inspecting transparent or translucent containers (3) traveling along a determined path $F_1$ at a high rate between a light source (7) and an image-taking system (9) for taking images of the containers and for analyzing the images taken, in order to determine as a characteristic of the container (3) at least the presence of a defect that refracts light or the quality with which the material constituting the container is distributed, the method being characterized by the following steps:

illuminating each container (3) traveling at a high rate by means of the light source (7) that presents light intensity variation in a periodic pattern ($7_1$) of period $T_1$ along at least a first variation direction (D);

for each container (3), taking a number N greater than or equal to three of images of the container traveling in front of the light source and occupying N different respective positions along the travel path;

between taking successive images, creating a relative shift between the container and the periodic pattern in a variation direction (D) of the periodic pattern ($7_1$);

determining and applying a geometrical transformation in at least N−1 images of the same container for at least a set of points belonging to the container in order to put the pixels belonging to the container in the N successive images of the same container into coincidence;

for each container (3) using the N registered images of the container, constructing a phase image; and analyzing the phase image in order to deduce therefrom, as a characteristic of the container (3), at least the presence of a defect that refracts light or the quality of the distribution of the material constituting the container.

2. A method according to claim 1, characterized by the following steps:

for each container (3), using the N registered images of the container to construct an intensity image; and analyzing the intensity image in order to deduce therefrom as a characteristic of the container (3), the presence of a defect that absorbs light and/or the dimensions of the container.

3. A method according to claim 1, characterized in that the analysis of the phase image consists in determining the speed and/or the amplitude of variation and in comparing said speeds and/or amplitudes with thresholds in order to determine the presence of a defect that refracts light or the quality of the distribution of the material constituting the container.

4. A method according to claim 1, characterized in that it consists in:

illuminating each container (3) to be inspected with the help of a light source (7) presenting light intensity variation in a periodic pattern of period $T_2$ in a second variation direction different from the first variation direction;

for each container, taking a number N greater than or equal to three of additional images of the article traveling in front of the light source and occupying three N respective different positions along the travel path;

between taking successive images, creating a relative shift between the container and the periodic pattern along the second variation direction of the periodic pattern of period $T_2$;

for each container, using the N registered images of the article to construct a second phase image; and analyzing the second phase image in order to determine, as a characteristic of the container (3) the presence of a defect that refracts light or the quality of the distribution of the material constituting the container.

5. A method according to claim 1, characterized in that it consists in selecting the period $T_1$, $T_2$ of the periodic pattern and the occurrences of the images taken in such a manner that the relative shifts of the container (3) and of the periodic pattern ($7_1$) along the variation direction of the periodic pattern are equal fractions of the period of the pattern under consideration.

6. A method according to claim 1, characterized in that it consists in obtaining the relative shift between the periodic pattern ($7_1$) and the containers (3) by the containers (3) traveling relative to the periodic pattern ($7_1$) that remains stationary.

7. A method according to claim 1, characterized in that it consists in obtaining the relative shift between the periodic pattern ($7_1$) and the containers (3) by causing the periodic pattern to shift between taking successive images.

8. A method according to claim 1, characterized in that it consists in triggering the taking of images and/or the shifting of the illumination pattern as a function of the positions of the containers (3) traveling relative to the image-taking system (9) so as to obtain predefined shifts.

9. A method according to claim 1, characterized in that it consists in selecting a periodic pattern ($7_1$) presenting a function in the variation in the level of the emitted light along the variation direction (D) that is sinusoidal.

10. A method according to claim 1, characterized in that it consists in positioning the periodic pattern in such a manner that a variation in light intensity occurs in at least one direction parallel to the travel direction of the containers.

11. A method according to claim 1, characterized in that it consists in selecting a periodic pattern that is rectilinear.

12. An installation for in-line inspection of transparent or translucent containers (3) in order to detect characteristics of the containers, the installation comprising conveyor means (2) for conveying the containers (3) so that they travel through an inspection station (5) made up of at least one light source (7) placed on one side of the traveling containers and at least one image-taking system (9) for taking images of the containers arranged on the other side of the containers, together with a unit for analyzing the images taken, the installation being characterized in that:

the light source (7) presents light intensity variation with a periodic pattern of period $T_1$ along at least a first variation direction (D);

a first image-taking system (9) is suitable for taking a number N greater than or equal to three of images of each container placed in front of the light source, with a relative shift being created between the container (3) and the periodic pattern ($7_1$) along a variation direction (D) of the periodic pattern ($7_1$) between taking successive images; and the control and processor unit (13) comprises:

means for determining and applying a geometrical transformation in at least N−1 images of the same container coming from the first image-taking system in order to put into coincidence pixels of the container in the N successive images of the same container as put into register in this way;

means for calculating at least one phase image from N registered images of the container; and means for analyzing the phase images in order to deduce therefrom, as a characteristic of the container, (3) at least the presence of a defect that refracts light or the quality of the distribution of the material constituting the container.

13. An inspection installation according to claim 12, characterized in that the control and processor unit (13) also includes means for calculating at least one intensity image from N registered images of the container obtained from the first image-taking system, and means for analyzing intensity images in order to deduce therefrom, as a characteristic of the container (3), the presence of a defect that absorbs light, and/or its dimensions.

14. An inspection installation according to claim 13, characterized in that it includes:

a filter interposed between the containers (3) and the light source (7) to polarize light linearly in a first polarization direction or circularly in a first direction of circular polarization;

a second image-taking system (9) suitable for taking a number N greater than or equal to three of images of each container placed in front of the light source;

a filter interposed between the containers and the second image-taking system for polarizing light linearly in the polarization direction orthogonal to the first or circularly in the direction of circular polarization that is opposite to the first; and a control and processor unit (13) comprising:

means for determining and applying a geometrical transformation in at least N−1 images of the same container coming from the first image-taking system in order to put into coincidence pixels of the container in the N successive images of the same container as put into register in this way;

means for calculating at least one intensity image from N registered images of the container coming from the second image-taking system; and means for analyzing the intensity images in order to deduce therefrom, as a characteristic of the container (3), the presence of a defect that modifies the polarization state of light.

15. An installation according to claim 12, characterized in that the periodic pattern ($7_1$) of the light source (7) is stationary, such that the relative shift between the periodic pattern ($7_1$) and the containers (3) is obtained by the containers (3) traveling relative to the periodic pattern ($7_1$).

16. An installation according to claim 12, characterized in that the periodic pattern ($7_1$) of the light source (7) is shifted between taking successive images in order to obtain the relative shifts between the periodic pattern ($7_1$) and the containers (3).

17. An installation according to claim 12, characterized in that the periodic pattern ($7_1$) of the light source (7) is positioned in such a manner that a variation in light intensity occurs along at least one direction parallel to the travel direction of the containers.

18. An inspection installation according to claim 12, characterized in that the light source (7) is suitable for presenting a periodic pattern (7) presenting a function for variation in the level of emitted light along its variation direction that is sinusoidal.

19. An inspection installation according to claim 12, characterized in that the image-taking system (9) is associated with synchronizing means in order to be triggered as a function of the positions of containers relative to the periodic pattern of the light source (7).

20. An inspection installation according to claim 12, characterized in that the control and processor unit (13) controls the light source (7) in such a manner that the periodic light pattern ($7_1$) is shifted in a given direction for taking each image.

* * * * *